(12) United States Patent
Graham et al.

(10) Patent No.: US 7,849,537 B2
(45) Date of Patent: Dec. 14, 2010

(54) EQUIPMENT SUPPORT HAVING ROTATABLE BUMPERS AND HOOKS

(75) Inventors: Mark Alan Graham, Springboro, OH (US); David C. Newkirk, Lawrenceburg, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 1098 days.

(21) Appl. No.: 10/575,403

(22) PCT Filed: Oct. 12, 2004

(86) PCT No.: PCT/US2004/033475

§ 371 (c)(1),
(2), (4) Date: Apr. 10, 2006

(87) PCT Pub. No.: WO2005/037342

PCT Pub. Date: Apr. 28, 2005

(65) Prior Publication Data

US 2007/0018058 A1    Jan. 25, 2007

Related U.S. Application Data

(60) Provisional application No. 60/592,556, filed on Jul. 30, 2004, provisional application No. 60/510,756, filed on Oct. 13, 2003.

(51) Int. Cl.
*A47C 31/00*    (2006.01)
(52) U.S. Cl. .................. 5/503.1; 248/222.11; 403/263
(58) Field of Classification Search .............. 5/503.1, 5/662, 658; 248/224.51, 298.1, 430, 222.11, 248/222.13; 403/314, 263, 409.1
See application file for complete search history.

(56) References Cited

U.S. PATENT DOCUMENTS

| | | | |
|---|---|---|---|
| 1,290,809 A | 1/1919 | Truax |
| 2,470,524 A | 5/1949 | Scudder |
| 2,673,771 A | 3/1954 | Krewson |
| 2,696,963 A | 12/1954 | Sheperd |
| 4,113,222 A | 9/1978 | Frinzel |
| 4,262,872 A | 4/1981 | Kodet |

(Continued)

FOREIGN PATENT DOCUMENTS

WO    WO 92/18085    10/1992

(Continued)

OTHER PUBLICATIONS

PCT International Search Report, dated Apr. 17, 2007, (3 pages).

(Continued)

*Primary Examiner*—Gwendolyn Baxter
(74) *Attorney, Agent, or Firm*—Barnes & Thornburg LLP

(57) ABSTRACT

A patient care equipment support includes an equipment supporting portion configured to support patient care equipment, and at least one arm pivotally coupled to the equipment supporting portion, and configured to support at least one IV container. The equipment support may include at least roller bumper rotatably coupled to the equipment supporting portion. The equipment supporting portion may include an upper horizontal member, a lower horizontal member and a pair of horizontally spaced vertical posts extending between the upper and lower members. Illustratively, the arm is pivotally coupled to one of the posts. The upper and lower horizontal members may define a space therebetween for receiving infusion management equipment.

23 Claims, 4 Drawing Sheets

U.S. PATENT DOCUMENTS

| | | | |
|---|---|---|---|
| 4,666,111 A | 5/1987 | Schuler | |
| 4,725,027 A | 2/1988 | Bekanich | |
| 4,795,122 A | 1/1989 | Petre | |
| 4,905,944 A | 3/1990 | Jost et al. | |
| 4,925,444 A | 5/1990 | Orkin et al. | |
| 4,945,592 A * | 8/1990 | Sims et al. | 5/658 |
| 5,026,017 A | 6/1991 | Kreuzer | |
| 5,078,349 A | 1/1992 | Smith | |
| 5,094,418 A | 3/1992 | McBarnes, Jr. et al. | |
| 5,112,019 A | 5/1992 | Metzler et al. | |
| 5,125,607 A | 6/1992 | Pryor | |
| 5,135,191 A | 8/1992 | Schmuhl | |
| 5,306,109 A | 4/1994 | Kreuzer et al. | |
| 5,337,992 A | 8/1994 | Pryor et al. | |
| 5,344,169 A | 9/1994 | Pryor et al. | |
| 5,366,191 A | 11/1994 | Bekanich | |
| 5,375,276 A | 12/1994 | Nelson et al. | |
| 5,400,995 A | 3/1995 | Boyd | |
| 5,407,163 A | 4/1995 | Kramer et al. | |
| 5,527,125 A | 6/1996 | Kreuzer et al. | |
| 5,527,289 A | 6/1996 | Foster et al. | |
| 5,618,090 A | 4/1997 | Montague et al. | |
| 5,647,491 A | 7/1997 | Foster et al. | |
| 5,876,016 A | 3/1999 | Urban et al. | |
| 5,915,659 A | 6/1999 | Scannell, Jr. | |
| 6,036,147 A | 3/2000 | Miilitzer | |
| 6,056,249 A | 5/2000 | Fillon, Jr. | |
| 6,109,572 A | 8/2000 | Urban et al. | |
| 6,375,133 B1 | 4/2002 | Morrow | |
| 6,390,311 B1 * | 5/2002 | Belokin | 211/204 |
| 6,431,505 B2 | 8/2002 | Chinn et al. | |
| 6,585,206 B2 | 7/2003 | Metz et al. | |
| 6,601,860 B2 | 8/2003 | Potter | |
| 6,619,599 B2 | 9/2003 | Elliott et al. | |
| 6,708,991 B1 | 3/2004 | Ortlieb | |
| 2004/0199996 A1 | 10/2004 | Newkirk et al. | |
| 2005/0000019 A1 | 1/2005 | Newkirk et al. | |

FOREIGN PATENT DOCUMENTS

| | | |
|---|---|---|
| WO | WO 00/09061 | 2/2000 |
| WO | WO2005/037164 | 4/2005 |

OTHER PUBLICATIONS

PCT Written Opinion of the International Searching Authority, dated Apr. 17, 2007, 4 pages).

* cited by examiner

EQUIPMENT SUPPORT HAVING ROTATABLE BUMPERS AND HOOKS

CROSS REFERENCE TO RELATED APPLICATIONS

This application is a U.S. national application under 37 C.F.R. §371(b) of International Application Serial No. PCT/US2004/033475 filed Oct. 12, 2004, which claims the benefit, under 35 U.S.C. §119(e), of U.S. provisional patent application Ser. No. 60/510,756 filed Oct. 13, 2003 and U.S. provisional patent application Ser. No. 60/592,556 filed Jul. 30, 2004, each of which is hereby expressly incorporated by reference herein.

FIELD OF THE INVENTION

The present disclosure relates to a patient care equipment support, and more particularly relates to a patient care equipment support, such as an IV rack, to support IV containers and infusion management equipment.

BACKGROUND OF THE INVENTION

In critical care situations, a patient care equipment support, such as an IV rack, is supported in close proximity to a patient in order to supply the patient with multiple fluids that may be required by the patient's condition. Such fluids may, for example, include antibiotics, nutrients and the like. In some critical situations, as many as twelve to fifteen IV infusions may be required.

SUMMARY OF THE INVENTION

The present invention comprises one or more of the following features or elements in the appended claims or combinations thereof.

A patient care equipment support comprises an equipment supporting portion configured to support patient care equipment, and at least one member rotatably coupled to the equipment supporting portion.

The at least one member may comprise an arm pivotally coupled to the equipment supporting portion to support one or more items of patient care equipment. Illustratively, the arm is configured to support at least one IV container. In some embodiments, the at least one member may comprise a pair of arms pivotally coupled to the equipment supporting portion near opposite ends thereof.

Alternatively, the at least one member may comprise a roller bumper rotatably coupled to the equipment supporting portion and having a peripheral portion extending horizontally beyond the equipment supporting portion. In some embodiments, the at least one member comprises a pair of roller bumpers rotatably coupled to the equipment supporting portion near the opposite ends thereof. The equipment supporting portion may defines a recess, and each arm may be configured to move between a retracted position within the recess and an extended position outside the recess.

Illustratively, each arm has a plurality of hook portions spaced therealong to support a plurality of IV containers. The plurality of hook portions may be spaced at equal increments along the length of the arms. Each hook portion may comprise a disc having a circular, elliptical, oval or non-round cross section. Each arm may have a plurality of outwardly extending portions, with each outwardly extending portion supporting a hook portion at a distal end thereof. Illustratively, the hook portion extends above and below the outwardly extending portion in a common plane.

The equipment supporting portion may include an upper horizontal member, a lower horizontal member and a pair of horizontally spaced vertical posts extending between the upper and lower members near the opposite ends thereof. Illustratively, the arms are pivotally coupled to the respective posts. Each arm may include a collar portion having a bore configured to receive one of the posts and a cantilevered portion extending outwardly. Illustratively, the cantilevered portions each has a plurality of hook portions spaced therealong to support a plurality of IV containers. The bore in the collar portion may be sized to provide a frictional engagement between the collar portion and the associated post.

Illustratively, each post has a circumferential groove positioned below the collar portion of the respective arm for receiving a retaining ring therein. In some embodiments, the collar portion is held between two retaining rings, one above and one below the collar portion. A spring, such as a wave washer, may be held in a state of compression between each collar portion and the associated retaining ring to provide a rotational drag on the respective arm.

Illustratively, the arms are located near the upper horizontal member. The upper and lower horizontal members may define a space therebetween configured to house infusion management equipment. The lower horizontal member may be configured to form a shelf or ledge to support infusion management equipment. In some embodiments, the equipment supporting portion may include a third vertical post extending between the upper and lower horizontal members and located between the two horizontally spaced vertical posts. The third vertical post may be adapted to support infusion management equipment.

Illustratively, the upper horizontal member may have a pair of roller bumper-receiving spaces near the opposite ends thereof. The roller bumpers may each have at least a portion thereof received in a respective one of the roller bumper-receiving spaces in the upper horizontal member.

The equipment support may include a coupler extending downwardly from the equipment supporting portion, and configured for receipt in a patient support, such as a hospital bed, or a support structure, such as a service column. The coupler may have an upper tapered portion, a lower tapered portion and a generally cylindrical intermediate portion disposed between the upper and lower tapered portions.

Although the illustrative patient care equipment support disclosed herein comprises an IV rack, the patient care equipment support may very well be configured to support any one or more of the following: heart monitoring equipment, medical gas delivery equipment, equipment monitors, patient monitors, defibrillators and the like, many of which are directly connected to a patient via lines or tubes.

Features of the present disclosure will become apparent to those skilled in the art upon consideration of the following detailed description of illustrative embodiments exemplifying the best mode of carrying out the present disclosure as presently perceived.

BRIEF DESCRIPTION OF THE DRAWINGS

The detailed description particularly refers to the accompanying figures, in which.

DESCRIPTION OF THE ILLUSTRATIVE EMBODIMENTS

For the purposes of promoting an understanding of the principles of the present invention, reference will now be made to a number of illustrative embodiments shown in the accompanying drawings and the following description thereof.

Figure 1:
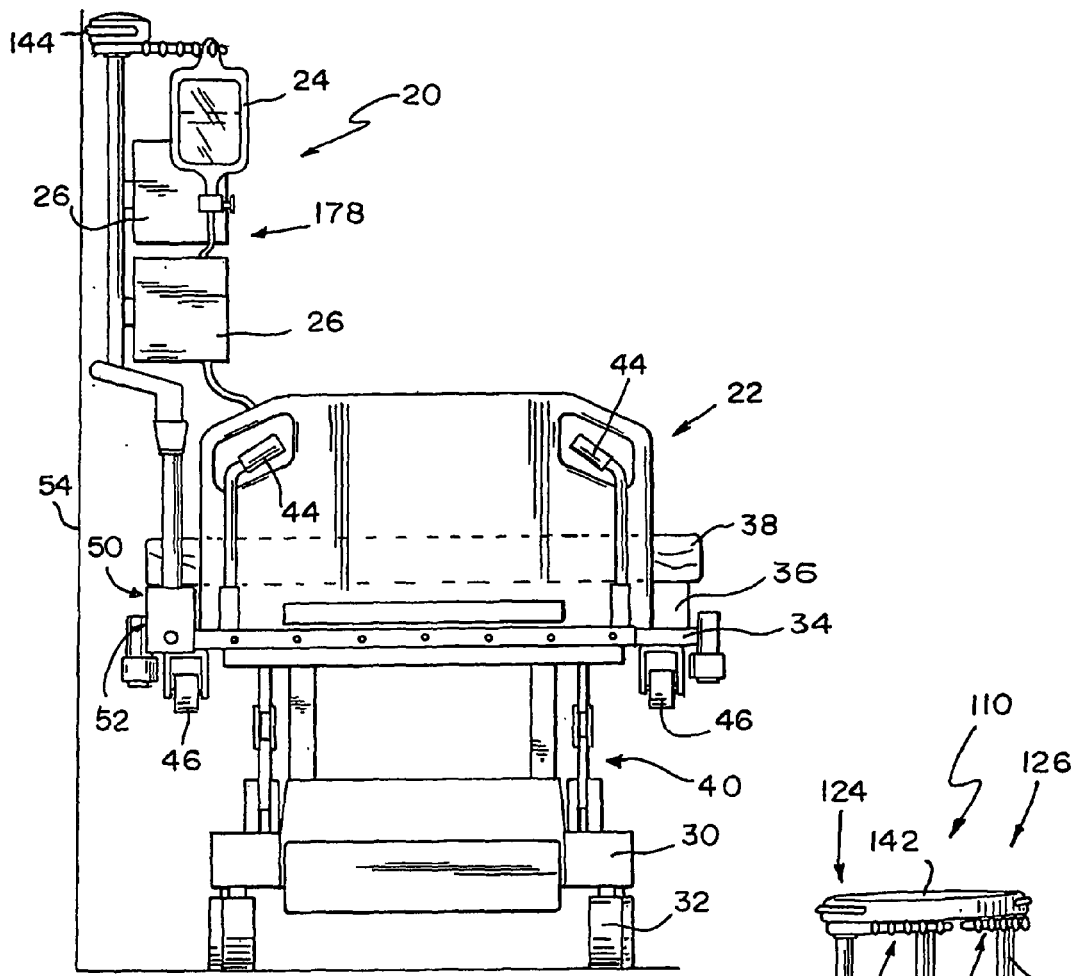
FIG. 1 is an end view of a patient care equipment support coupled to a patient support.
Figure 2:
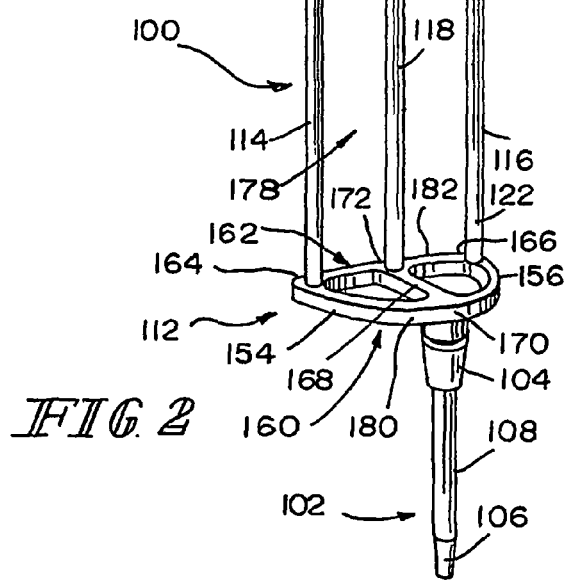
FIG. 2 is a perspective view of the patient care equipment support of FIG. 1.

FIG. 1 shows a patient care equipment support, such as an IV rack 20, coupled to a patient support, such as a hospital bed 22. The IV rack 20 is configured to support a plurality of IV containers 24, such as IV bags or bottles, and infusion management equipment 26, such as infusion pumps, monitors and controllers. Referring to FIG. 2, the patient care equipment support 20 includes an equipment supporting portion 100 and a coupler 102 extending downwardly from the equipment supporting portion 100.

The coupler 102 includes an upper tapered portion 104, a lower tapered portion 106 and a generally cylindrical intermediate portion 108 disposed between upper and lower tapered portions 104, 106. The upper tapered portion 104 varies in diameter from a large diameter to a small diameter in a downward direction. Likewise, the lower tapered portion 106 varies in diameter from a large diameter to a small diameter in downward direction. Illustratively, the small diameter of the upper tapered portion 104 is equal to or larger than the large diameter of the lower tapered portion 106. The diameter of the cylindrical intermediate portion 108 is equal to or smaller than the small diameter of the upper tapered portion 104 and equal to or larger than the large diameter of the lower tapered portion 106.

The two stage coupler 102 facilitates transfer of the equipment support 20 between a support structure having an upper tapered socket (not shown) for receiving the upper tapered portion 104 of the coupler 102 when the equipment support 20 is supported by the support structure and the hospital bed 22 having a lower tapered socket 52 for receiving the lower tapered portion 106 of the coupler 102 when the equipment support 20 is supported by the hospital bed 22. The support structure may comprise a service column, a radial arm, a floor-supported stand, a wheeled car, a headwall, a wall of a hospital room and the like. The upper socket has an outwardly opening slot to allow the support structure to pull away from the equipment support 20 after the equipment support 20 is firmly seated in the lower socket 52 and the upper socket is lowered to a position below the upper portion 104. PCT international application publication no. WO 2004/082553 published Sep. 30, 2004, discloses an illustrative service column and is incorporated by reference herein.

The hospital bed 22 illustratively includes a lower frame 30 supported on casters 32, an upper frame 34 supported above the lower frame 30 for movement relative to the lower frame 30 between raised and lowered positions, a deck 36 supported above the upper frame 34, and a mattress 38 supported by the deck 36. An elevation adjustment mechanism 40 connects the upper frame 34 to the lower frame 30. The elevation adjustment mechanism 40 may be driven by a suitable actuator to cause the upper frame 34 to move relative to the lower frame 30. The upper frame 34 includes a head-end frame member 42 configured to extend transversely along the head end of the upper frame 34 beyond the outer periphery of the deck 36. The head-end frame member 42 supports push handles 44 and rolling bumpers 46.

A transversely extending rail 48 is supported by the frame member 42. A carriage 50, carrying the lower socket 52, is coupled to the rail 48 for movement along rail 48. The lower socket 52 has an upwardly opening frustoconical bore for receiving the lower tapered portion 106 of the coupler 102 when the equipment support 20 is supported by the hospital bed 22. The frustoconical bore in the lower socket 52 varies in diameter from a large diameter to a small diameter in a downward direction. The carriage 50 is lockable at any one of a plurality of locations along the rail 48. Illustratively, PCT international application publication no. WO 2005/037164 discloses such hospital bed and is incorporated by reference herein.

Although the illustrative patient care equipment support in FIG. 1 is the IV rack 20 to support IV containers 24 and infusion management equipment 26, the patient care equipment support may very well be configured to support one or more of the following: heart monitoring equipment, medical gas delivery equipment, equipment monitors, patient monitors, defibrillators, and the like, many of which are directly connected to a patient via lines or tubes. Likewise, although the patient support illustrated in FIG. 1 is the hospital bed 32, the patient support may very well be a stretcher, a surgical table, an ambulatory care chair, and the like.

As shown in FIG. 2, the equipment support 20 includes an upper horizontal member 110, a lower horizontal member 112, a pair of vertical posts 114, 116 near opposite ends 124, 126 of the upper and lower horizontal members 110, 112 and a vertical post 118 positioned midway between the outer posts 114, 116. Each vertical post 114-118 has an upper end portion 120 secured to the upper horizontal member 110 and a lower end portion 122 secured to the lower horizontal member 112. Suitable fasteners, such as pins, studs, threaded screws and the like, may be used for securing the posts 114-118 to the upper and lower horizontal members 110, 112.

Figure 3:
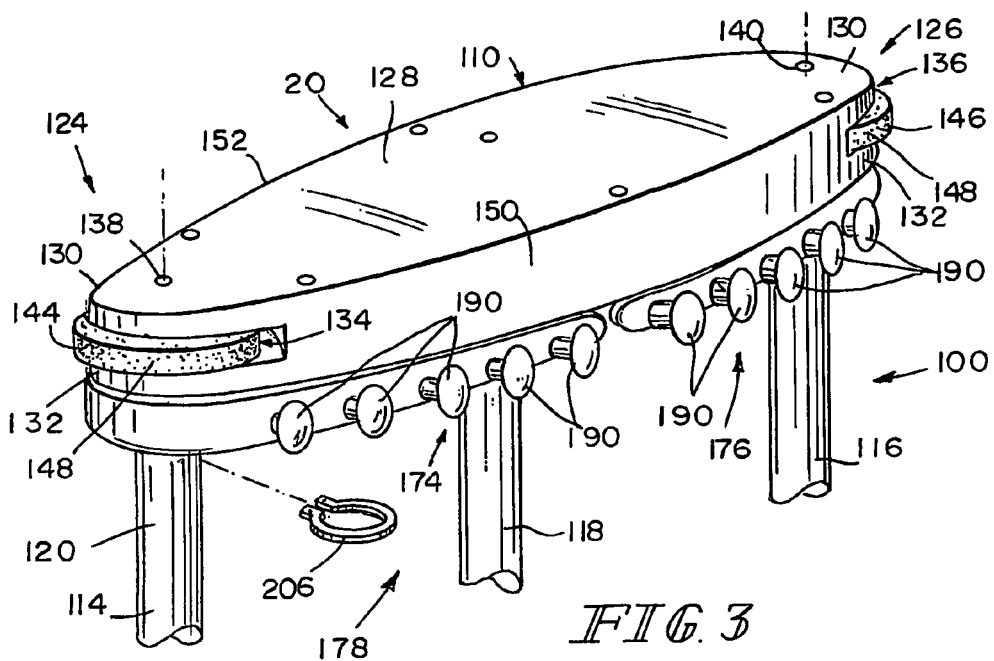
FIG. 3 is an enlarged partial perspective view of the patient care equipment support of FIGS. 1 and 2.
Figure 4:
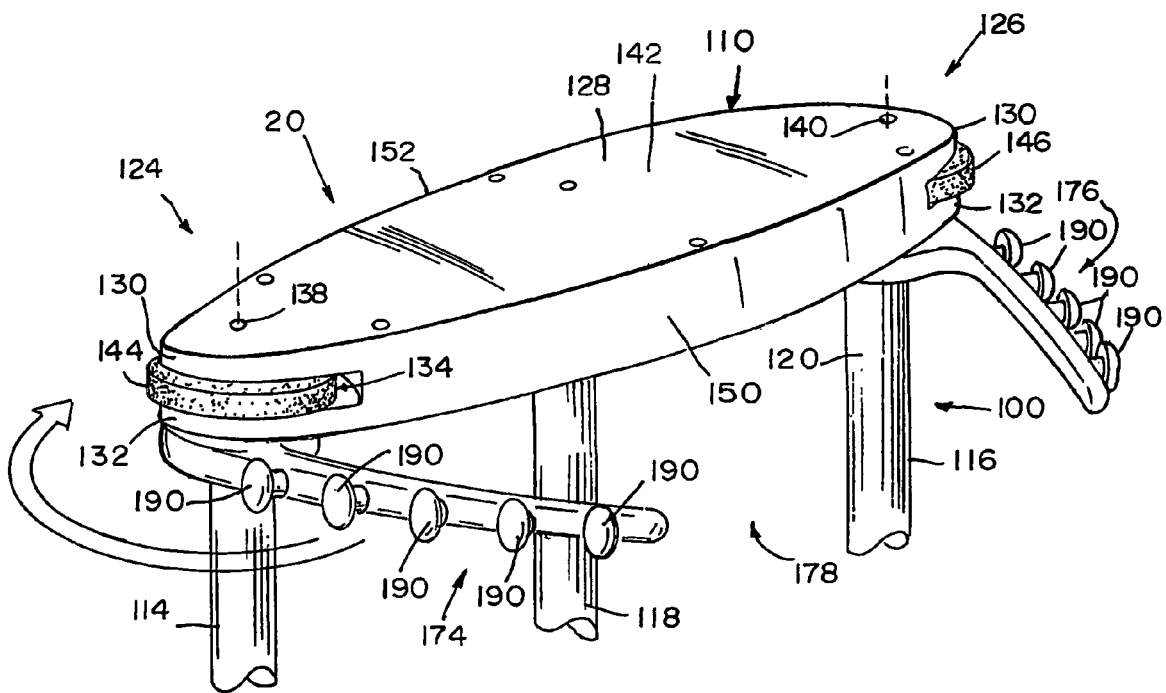
FIG. 4 is an enlarged partial perspective view similar to FIG. 3.

As shown in FIGS. 3 and 4, the illustrative upper horizontal member 110 has generally curved front and rear walls 150, 152. The upper horizontal member 110 has a main body portion 128 and a pair of vertically spaced flange portions 130, 132 extending outwardly from the main body portion 128 near the opposite ends 124, 126 of the upper horizontal member 110 to define a pair of roller bumper-receiving spaces 134, 136, respectively. A pair of roller bumpers 144, 146 are rotatably mounted in the two roller bumper-receiving spaces 134, 136 by respective pins 138, 140. Alternatively, the roller bumpers 144, 146 may be supported by the upper ends 120, 122 of the posts 114, 116. To this end, the roller bumpers 144, 146 may have central bores (not shown) configured for receiving the upper ends 120, 122 of the posts 114, 116 that extend into the respective one of the roller bumper-receiving spaces 134, 136. Each roller bumper 144, 146 has a peripheral portion 148 that extends horizontally beyond the outer periphery of the upper horizontal member 110. The peripheral portions 148 of the roller bumpers 144, 146 may be made from soft rubber or plastic material to prevent the equipment support 20 from scraping or denting the walls, such as a wall 54, of the hospital as the hospital bed 22 carrying the equipment support 20 is moved around in the hospital.

Referring to FIG. 2, the lower horizontal member 112 has generally curved front and rear frame members 160, 162 and a cross frame member 168 extending between the front and rear frame members 160, 162. The front frame member 160 has end portions 154, 156 coupled to end portions 164, 166 of the rear frame member 162. The cross frame member 168 extends between central portions 170, 172 of the front and rear frame members 160, 162, respectively. The rear walls 152, 182 of the upper and lower horizontal frame members 110, 112 have generally matching profiles and a common footprint. However, the front wall 180 of the lower horizontal member 112 projects forwardly of the front wall 150 of the upper horizontal member 110. The coupler 102 extends downwardly from the underside of the front frame member 160 and positioned midway between the end portions 154, 156 of the front frame member 160.

The outside posts 114, 116 extend between the flange portions 132 of the upper horizontal member 110 and the end portions 164, 166 of the lower horizontal member 112, respectively. The central post 118 extends between the central portion 142 of the upper horizontal member 110 and the central portion 172 of the lower horizontal member 112. As shown in FIG. 1, the central post 118 is configured to support the infusion management equipment 26 in a space 178 defined by the upper and lower horizontal members 110, 112. The central post 118 carrying the infusion management equipment 26 is offset rearwardly with respect to the coupler 102 supporting the equipment support 20 relative to a hospital bed 22 or a support structure to ensure that the center of gravity of the infusion management equipment 26 is generally above the coupler 102.

Figure 5:
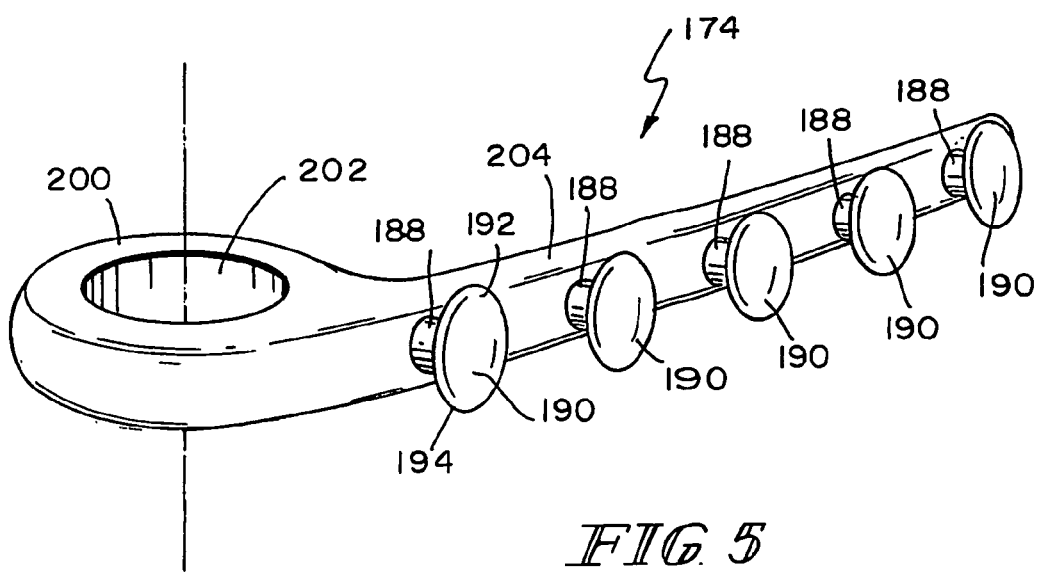
FIG. 5 is a perspective view of one of the arms.

Referring to FIGS. 3-5, the equipment support 20 includes a pair of arms 174, 176 pivotally coupled to the posts 114, 116 near the upper horizontal member 110. Each arm 174, 176 is movable between a retracted position within the space 178 as shown in FIG. 3 and an extended position outside the recess 178 as shown, for example, in FIG. 4. Each arm 174, 176 has a plurality of horizontally outwardly extending portions 188. Each outwardly extending portion 188 carries a hook portion 190 at a distal end thereof to support an IV container 24, such as an IV bag or a bottle. The arms 174, 176 can be rotated to any number of positions to allow positioning of the IV bags 24 in a variety of locations. Each hook portion 190 comprises a disc having a circular, elliptical, oval or non-round cross section.

Each hook portion 190 has portions 192, 194 that extend above and below the associated outwardly extending portion 188 in a common plane. The extension of hook portions 190 above and below the associated outwardly extending portions 188 improves the retention of the IV bags 24 and reduces the risk of accidental removal of the IV bags 24. The arms 174, 176 are symmetrical about a horizontal plane bisecting the vertical dimension of the arms 174, 176. This allows the same part to be used at both ends of the equipment support 20, which is a cost advantage.

Figure 7:
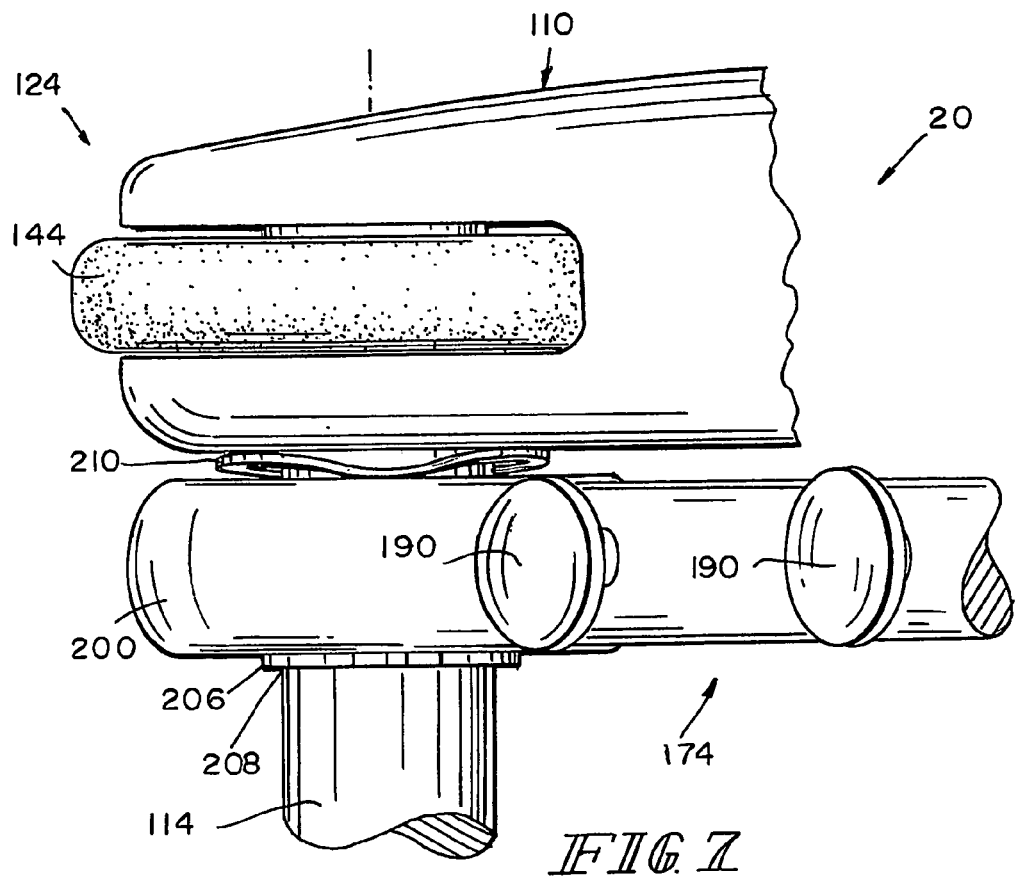
FIGS. 7 and 8 show construction details.

FIG. 5 shows one of the two arms 174, 176—namely, the arm 174. The other arm 176 is identical. The arm 174 includes a collar portion 200 having a bore 202 configured to receive the associated post 114, 116 and a cantilevered portion 204 extending outwardly from the collar portion 200. Each bore 202 in the collar portion 200 is dimensioned to provide a snug fit with the associated post 114, 116. Referring to FIG. 7, each collar portion 200 is held between the underside of the upper horizontal arm 110 and the topside of a retaining ring 206 received in a circumferential groove 208 in the associated post 114, 116. A wave washer 210 is held in a state of compression between each collar portion 200 and the associated retaining ring 208 to provide a rotational drag on the respective arm 174, 176.

Figure 8:
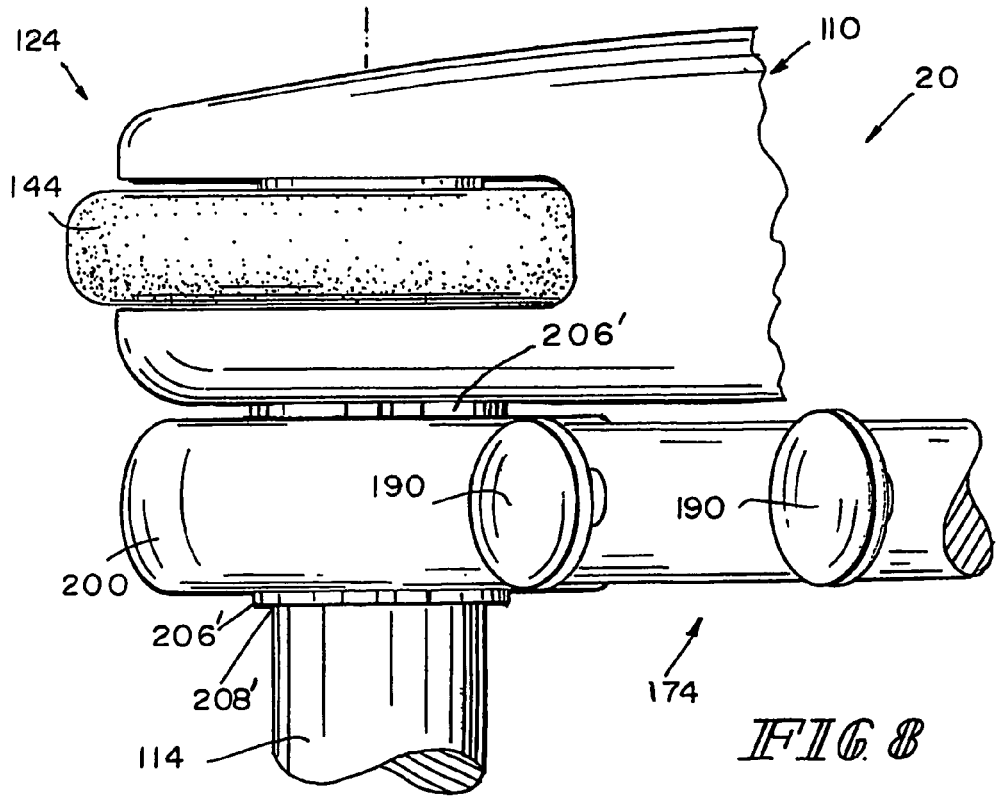

Alternatively, as shown in FIG. 8, the arms 174, 176 may be held between a pair of retaining rings 206' received in associated grooves 208' in the posts 114, 116—one above and one below the associated collar portion 200. An upper wave washer (not shown) may be held in a state of compression between the topside of the collar portion 200 and the underside of the upper retaining ring 206'. A lower wave washer (not shown) may be held in a state of compression between the underside of the collar portion 200 and the topside of the lower retaining ring 206'.

Figure 6:
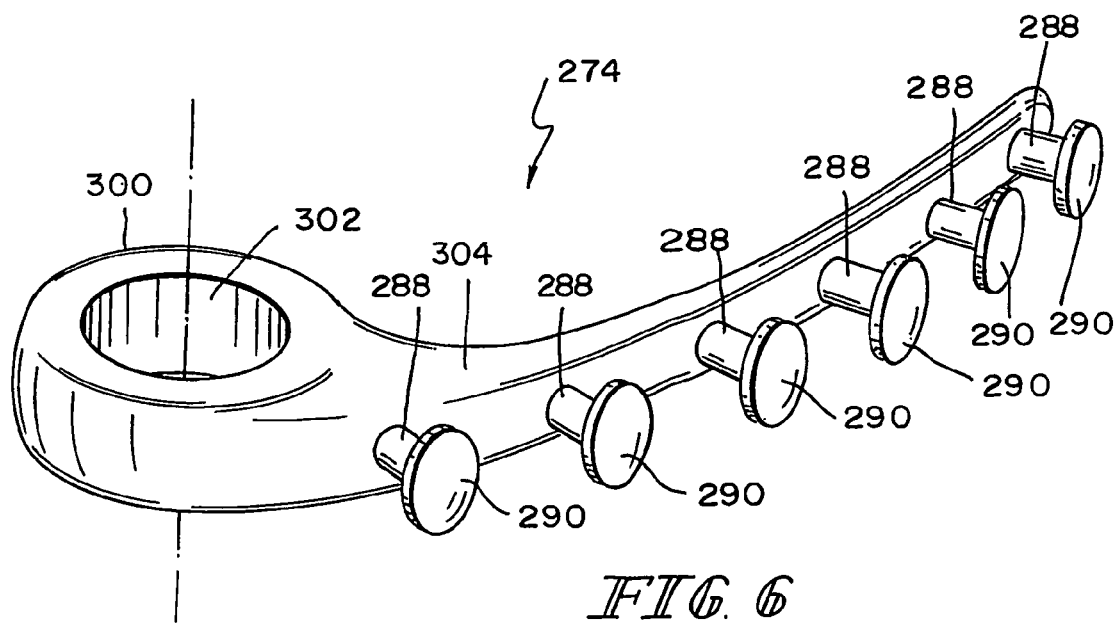
FIG. 6 is a perspective view of another embodiment of the arm.

FIG. 6 shows another embodiment 274 of the arm 174. Like elements in the two embodiments have like reference numerals. Thus, the arm 274 has a collar portion 300, bore 302, cantilevered portion 304, horizontally extending portions 288 and hook portions 290. The arm 274 has six hook portions 290 instead of five and a slightly different profile as viewed from the top to match the profile of the associated equipment support (not shown).

Reference is made to U.S. provisional patent application Ser. No. 60/592,617 filed Jul. 30, 2004, which discloses an equipment support having hook portions only at the ends of the rods, instead of having a plurality of hook portions 190 along the respective lengths of the rods 174, 176 as shown in FIGS. 1-8 herein, and is incorporated by reference herein.

Although the invention has been described in detail with reference to certain illustrative embodiments, variations and modifications exist with the scope and spirit of this disclosure as described and defined in the following claims.

The invention claimed is:

1. A patient care equipment support comprising:
   an equipment supporting portion configured to support patient care equipment,
   at least one member rotatably coupled to the equipment supporting portion, and
   a coupler coupled to the equipment supporting portion and extending generally downwardly therefrom, wherein the equipment supporting portion includes an upper member, a lower member and a pair of vertical posts extending between the upper and lower members, and the at least one member is pivotally coupled to one of the posts adjacent to the upper member.

2. The equipment support of claim 1, wherein the at least one member comprises an arm pivotally coupled to the equipment supporting portion, and the arm is configured to support at least one IV container.

3. The patient care equipment support of claim 1, wherein the at least one member comprises a roller bumper.

4. The equipment support of claim 1, wherein the at least one member comprises a pair of roller bumpers rotatably coupled to the equipment supporting portion.

5. The equipment support of claim 4, wherein the equipment supporting portion has upper and lower members, the roller bumpers are coupled to the upper member adjacent to opposite ends thereof, and each roller bumper has a peripheral portion that extends horizontally beyond the outer periphery of the equipment supporting portion.

6. The equipment support of claim 5, wherein the upper member has a pair of roller bumper-receiving spaces adjacent to the opposite ends thereof, and at least a portion of each of the roller bumpers is received in a respective one of the roller bumper-receiving spaces in the upper member.

7. A patient care equipment support comprising:
   an equipment supporting portion configured to support patient care equipment, and
   at least one member rotatably coupled to the equipment supporting portion, wherein the at least one member comprises a pair of arms pivotally coupled to the equipment supporting portion adjacent to opposite ends thereof, and each arm is configured to support at least one IV container, wherein the equipment supporting portion includes an upper member, a lower member and a pair of vertical posts extending between the upper and lower members, and the arms are pivotally coupled to the respective posts.

8. The equipment support of claim 7, wherein the equipment supporting portion defines a recess, and each arm is movable between a retracted position within the recess and an extended position outside the recess.

9. The equipment support of claim 7, wherein each arm has a plurality of hook portions spaced therealong to support a plurality of IV containers.

10. The equipment support of claim 9, wherein the plurality of hook portions are spaced at equal increments along the length of the respective arm.

11. The equipment support of claim 9, wherein each hook portion comprises a disc.

12. The equipment support of claim 11, wherein each disc is circular in cross section.

13. The equipment support of claim 11, wherein each disc is elliptical in cross section.

14. The equipment support of claim 11, wherein each disc is oval in cross section.

15. The equipment support of claim 7, wherein each arm has a plurality of outwardly extending portions extending outwardly, each outwardly extending portion carries a hook portion at a distal end thereof, and the hook portion extends above and below the outwardly extending portion in a common plane.

16. The equipment support of claim 7, wherein each arm includes a collar portion having a bore configured to receive one of the posts and a cantilevered portion extending outwardly from the collar portion.

17. The equipment support of claim 16, wherein each bore in the collar portion is dimensioned to provide a frictional engagement with the associated post.

18. The equipment support of claim 16, wherein each post has a groove positioned below the collar portion of the respective arm for receiving a retaining ring therein for vertically supporting the arm.

19. The equipment support of claim 18, comprising a wave washer held in a state of compression between each collar portion and the associated retaining ring to provide a rotational drag on the respective arm.

20. The equipment support of claim 7, wherein the arms are located adjacent to the upper member.

21. The equipment support of claim 7, wherein the posts are located adjacent to opposite ends of the upper and lower members.

22. The equipment support of claim 7, wherein the upper and lower members define a space therebetween to house infusion management equipment.

23. The equipment support of claim 7, wherein the equipment supporting portion includes a third vertical post extending between the upper and lower members and positioned between the two horizontally spaced vertical posts, and the third vertical post is configured to support infusion management equipment.

* * * * *